US005681950A

United States Patent [19]
Echeverri-Lopez et al.

[11] Patent Number: 5,681,950
[45] Date of Patent: Oct. 28, 1997

[54] WITHAJARDINS

[75] Inventors: Luis F. Echeverri-Lopez, Enuigado; Luis F. Torres-Roldán, Medellín; Luis F. Garcia-Moreno, Enuigado; Gloria Cardona-Rendón; Winston Quiñones-Fletcher, both of Medellín, all of Colombia; Javier Gutiérrez-Luis, Sta. Cruz de Tenerife; Antonio González-González, La laguna, both of Spain; Carlos A. Peláez-Jaramillo, Medellín; Mauricio Rojas-López, Envigado, both of Colombia

[73] Assignees: Universidad De Antioquia, Medellin; Colciencias, Santafe De Bogota, both of Colombia

[21] Appl. No.: 314,603

[22] Filed: Sep. 28, 1994

[51] Int. Cl.$^6$ ............................ C07J 71/00; C07J 17/00
[52] U.S. Cl. ................................................ 540/80; 540/103
[58] Field of Search ................................ 540/80, 103

[56] References Cited

U.S. PATENT DOCUMENTS 5,494,668  2/1996  Patwardhan ...................... 424/195.1

OTHER PUBLICATIONS

Kirson et al. "Recent Developments in Naturally Occurring Ergostane-Type Steroids", *Jnl. of Natural Products*, 44:633–647 (1981).
Glotter "Withanolides and Related Ergostane–type Steroids", *Natural Product Reports*, 8:415–440 (1991).
Ksebati et al. "Minabeolides: A Group of Withanolides from a Soft Coral, *Minabea sp.*", *Jnl. Org. Chem.*, 53:3926–3929 (1988).
Kupchan et al. "Tumor Inhibitors. XXXIX. Active Principles of *Acnistus arborescens*. Isolation and Structural and . . . ", *Jnl. Org. Chem.*, 34:3858–3866 (1969).
Suffness et al. "Current Status of the NCI Plant and Animal Product Program", *Jnl. of Natural Products*, 45:1–14 (1982).
Shohat et al. "Immunosuppressive Activity of Two Plant Steriodal Lactones Withaferin A and Withanolide E", *Biomedicine*, 28:18–24 (1978).
Budhiraja et al. "Anti–inflammatory Activity of 3 β–Hydroxy–2,3–dihydro–withanolide F", *Planta Medica*, 134–136 (1984).
Budhiraja et al. "Protective Effect of 3 β–Hydroxy–2,3–dihydrowithanolide F Against $CCl_4$–induced Hepatotoxicity", *Planta Medica* 28–29 (1986).
Kawai et al. "Physalins N and O From *Physalis Alkekengi*", *Phytochemistry*, 31:4299–4302 (1992).
Luis et al. "Withajardins, Withanolides with a New Type of Skeleton Structure of Withajardins A, B, C and D Absolute Configuration of Withajardin C", *Tetrahedron*, 50:1217–1226 (1994).
Gutierrez et al. Abstract—"The Structure of Withajardins B, C, D and E".
Echeverri et al. Abstract—"Immunomodulatory Activity of Withajardin A".
Echeverri et al., Structure of Withajardin B, Spectroscopy, vol. 7 (5–6), pp. 345–352 (1989).
Echeverri et al., Withajardin: A new type of withanolides, Spectroscopy Internation Journal, vol. 6, pp. 137–146 (1988).

*Primary Examiner*—Mukund J. Shah
*Assistant Examiner*—Deepak R. Rao
*Attorney, Agent, or Firm*—Foley & Lardner

[57] ABSTRACT

Withajardins A–D are new class of withanolides isolated from the leaves of *Deprea orinocensis* and characterized by having a bicyclic C-17β system and hydroxyl group at C-14 and C-17. The bicyclic system consists of a lactone and a homocyclic ring with six carbon atoms unlike the acnistins which have a five-membered homocyclic ring. The two classes of compounds were differentiated and their structures were identified by a series of HMQC, HMBC and finally X-ray diffraction experiments. Withajardins and acnistins would seem to evolve along quite dissimilar biosynthetic pathways although both types of compound show a marked immunosupressive effect on in vitro cultures of human lymphocytes.

9 Claims, 10 Drawing Sheets

0# WITHAJARDINS

BACKGROUND OF THE INVENTION

Withanolides belong to a group of steroids that have been so far isolated only from plants of the family Solanaceae and specifically from genera Withania, Dunalia (Acnistus), Datura, Jaborosa, Witheringia, Physalis, Deprea and Nicandria. In chemical taxonomy, these compounds are important since their presence excludes the steroidal alkaloids; chemically, they are very interesting due to the high content of oxygen and to the existence of a lactonic chain at $C_{17}$.

Our interest in the study of the chemistry and biological effects of whithanolides is based on: 1-Colombia is very rich in different species of Solanaceae but unfortunately little is known on their chemical and biological properties. 2-Throughout the world the world there are many folk applications of these plants, their extracts are used in asthma, hepatic diseases, different inflammatory processes and cancer, and even as a hypnotic drug. Some of these properties have been experimentally confirmed.

SUMMARY OF THE INVENTION

Withajardin A, B, C and D, and derivatives thereof are withanolides isolated from leaves and stems of *Deprea orinocensis*. Withajardin A, B, C and D, and derivatives thereof, are steroids having a hinge oxygen content and a lactonic chain at $C_{17}$ and an α,β-unsaturated ketone in ring A. These compounds can be used as immunomodulators of the immune system. At low concentrations, withajardin A stimulates mitogen or antigen-induced lymphocyte proliferation. At higher concentrations withajardin A, B, C and D, and derivatives thereof, cause immunosuppression.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION

The present molecules, which have an α-β unsaturated system in the ring A, are particularly interesting due to their application as immunomodulatory agents as demonstrated by the in vitro experiments described below. These substance could have applications as tools to study the cellular and molecular phenomena that occur during the immune response. Pharmacologically they could be used as immunomodulators of the immune response. At low concentrations they stimulate mitogen or antigen-induced lymphocyte proliferation whereas at higher concentrations they exhibit inhibitory activity, suggesting that a low doses they could be used as immunopotentiator in immunodeficiencies such as AIDS, and at high doses they could be used in immunosupression for organ transplantation or autoimmune diseases.

The withajardins are a group of steroid lactones with a withanolide skeleton which have a bicyclic 17-α side chain. They have been isolated from the leaves of *Deprea orinocensis* and their structure was established by 2D-NMR, HREIMS and X-ray diffraction analysis. Withajardin A was the major product and exhibited interesting immunomodulatory activity in in vitro assays on human lymphocytes. A dose of 0.01 µg/ml potentiated [$^3$H]-thymidine uptake, an effect confined almost exclusively to T lymphocytes. These results were further corroborated by treatment with PPD and one-way expenmenus. After treatment with Withajardin A cellular viability was still close to the 100% level, thus ruling out possible cytoxicity. Withajardin A, B, C, and D have similar immunosuppressive activity at concentrations of approximately 1 µg/ml or greater.

The withanolides are a group of steroid lactones which have been isolated from several genera of Solanaceae[1,2] and recently have also been found in a soft coral[3]. Several of these substances have displayed various types of biological activity, such as cytotoxic[4], anticancer[5], immunosuppresive[6], anti-inflammatory[7], and hepatoprotective[8] properties.

The withanolides are characterized chemically by a lactone chain at C-17 and different oxidations, mainly in the A, B and E rings[2]. However, biogenetic transformations can produce very modified compounds such as the physalins[9], trechonolide[10], prejaborol[11], withamelins[12] and acnistins[13]. In the course of a biological screening we studied the species *Dunalia solanaceae*[14], finding acnistins A and E. New withajardins A, B, C and D, with a new skeleton related to that of the acnistins, were found from the leaves of *Deprea orinocensis*.

Withajardins A–D have the structures IA–ID:

IA R = OH
ID R = OAc

IB R = OH
IC R = OAc

Withajardins can have limited structural variability in the A/B ring system without loss of immunomodulatory activity. In particular, the substituent R at C4 can be hydroxy, lower alkoxy, lower acyloxy or lower alkyl. In general, lower alkoxy will include straight or branched $C_{1-6}$-alkoxy, lower acyloxy will include $C_{1-6}$-acyloxy and lower alkyl will include $C_{1-6}$-alkyl, with the smallest groups being preferred over the larger. Preferred compounds will be those wherein R is hydroxy or acetyl. Other preferred compounds include those wherein R is methyl or methoxy or ethoxy.

Esterification of compounds with OH at C4 proceeds in the cold and is selective for the equatorial 4β-OH. Typically, acetic anhydride, with a catalytic amount of pyridine, in tetrahydrofuran, at about 0° C. is effective.

The structures of acnistins A and E have recently been studies[14] by 2D-NMR. Starting the analysis of the HMBC spectrum at the lactone carbonyl, easily identified by its shifts at 178.92 and 179.09 ppm, respectively. In this way, sequentially following the two and three-bond correlations, the chemical shifts of the bicyclic side-chain could be unambiguously assigned as could the rest of the steroid system. Furthermore, the structure of acnistin D was confirmed by X-ray diffraction analysis, enabling its absolute configuration to be established. The application of these bidimensional techniques to acnistin E (with a structure earlier determined by X-ray diffraction[13]) and to 3-methoxy-acnistin E provided conclusive proof of the validity of the assignments.

Figure 2:
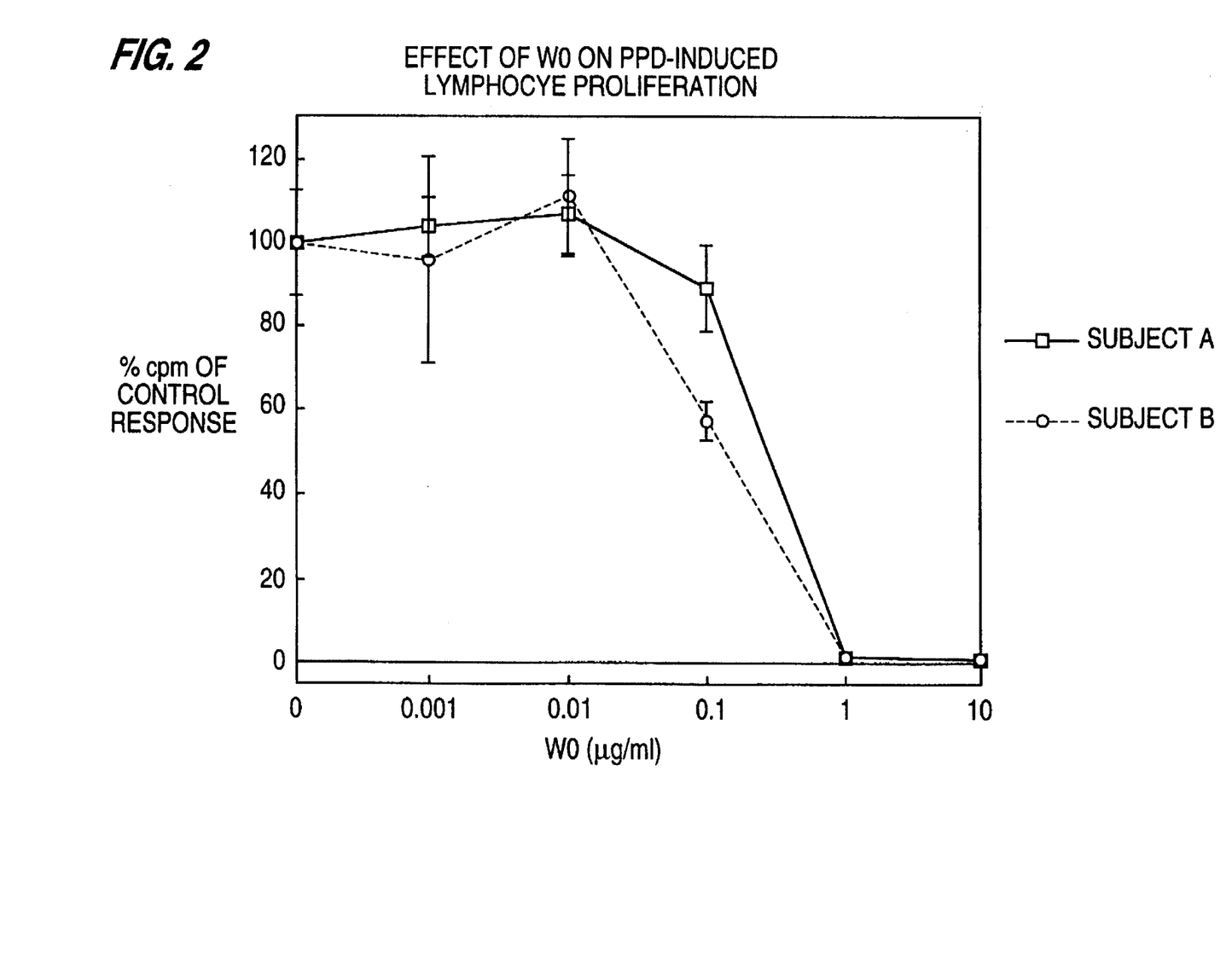
FIG. 2 is a graph showing the effect of a series of concentrations of Withajardin A ("WO") on PPD-induced lymphocyte proliferation in PBLs from two patients suffering from tuberculosis infection (i.e., lymphocytes sensitized to the effects of PPD). Concentrations of Withajardin A ("WO") are displayed along the horizontal axis in micrograms per milliliter ("µg/ml"). Proliferative activity is measured by incorporation of $^3$H-thymidine. in counts per minute ("cpm"), displayed along the vertical axis.

The chemical shifts of carbon atoms of the three acnistins were then compared with those found for withajardins A–D (FIG. 2) and from these data it would appear that a homocyclic five-membered side-chain ring was present as in the acnistins. Nonetheless, some discrepancies were observed for the shifts of the atoms C-20, C-22, C-24, C-25, C-27 and C-28, in particular (Table 1). HMBC[15] and HMQC[16] experiments on the four withajardins enabled their structures to be established conclusively and an X-ray diffraction analysis of the withajardin C established its absolute configuration. It was thus ascertained that the withajardins have a new carbon skeleton with a homocyclic six membered side chain ring.

Withajardin C (4), $C^{30}H^{40}O^{9}$ (Table II) has an α,β-unsaturated carbonyl in which the olefin protons form part of an AMX system as can be deduced from the $^1H$—$^1H$ COSY spectrum since a doublet is seen at 7.00 ppm (J=6.0 Hz and 9.8 Hz), a doublet at 6.25 (J=9.8 Hz) and another one at 4.26 ppm (J=6.0 Hz); the presence of an aceinte and an epoxide were deduced from the singlet at d 2.06 (3H) and d 3.24 (1H) (Table III).

The DEPT spectrum of withajardin C (4) Table I) indicates three carbonyls at 201.10, 178.37 and 170.1 ppm (the latter corresponding to the acetate), five oxygenated carbons, two of which are attributed to an epoxide (60.91) s and (60.73) d, five methyls (one the acetate methyl) and an oxygenated methine among other signals. HMQC established that the oxygenated methine corresponds to C-22 which is shown in $^1H$ NMR as a doublet shifted to b 4.62 (J=1.7Hz) and in $^{13}C$ NMR as a doublet at 77.76[17,18]. Using a combination of HMQC and HMBC (Table IV) and starting from the lactone carbonyl at 178.37 three bond correlations could be observed with Hj-22, H-27 and H-21ax; the latter is also coupled with C-17 and an oxygenated quaternary carbon at 70.37 ppm which was assigned to C-24 since this is also connected by two and three bonds to H-23ax and H-28. The latter correlation is very significant as it places a hydroxyl γ to the lactone carbonyl and so the homocyclic system closure is the side chain could be established between C-21 and C-25 and not between C-21 adn C-24 as in the acnistins. This fact was confirmed beyond possibility of doubt by the two and three bond correlations observed for C-20, C-24, C-25 and those for H-27 and H-28. These observations also hold good for the side chain of the withajardins A, B and D (Table IV).

The hydroxylations sites were also easy to deduce by HMBC; one was established at C-14 by correlation with Me-18 and another at C-17 by connection with the C-18, C-20 and C-21 protons. The acetate group was positioned at C-4 given the correlations of the acetate methyl with C-4 and C-4 with the H-4 with the carbonyl at C-4. Similarly, the epoxide could be sited between C-5, C-6. In the same way, connectivities between the other atoms in the molecule could be established (Table IV).

The relative configurations was deduced from the analysis of the ROESY spectrum of withajardins A–D in which effects between Hj-4 and H-6, H-8 and H-19 and H-23ax and H-18 among others could be appreciated (Table V).

Figure 3:
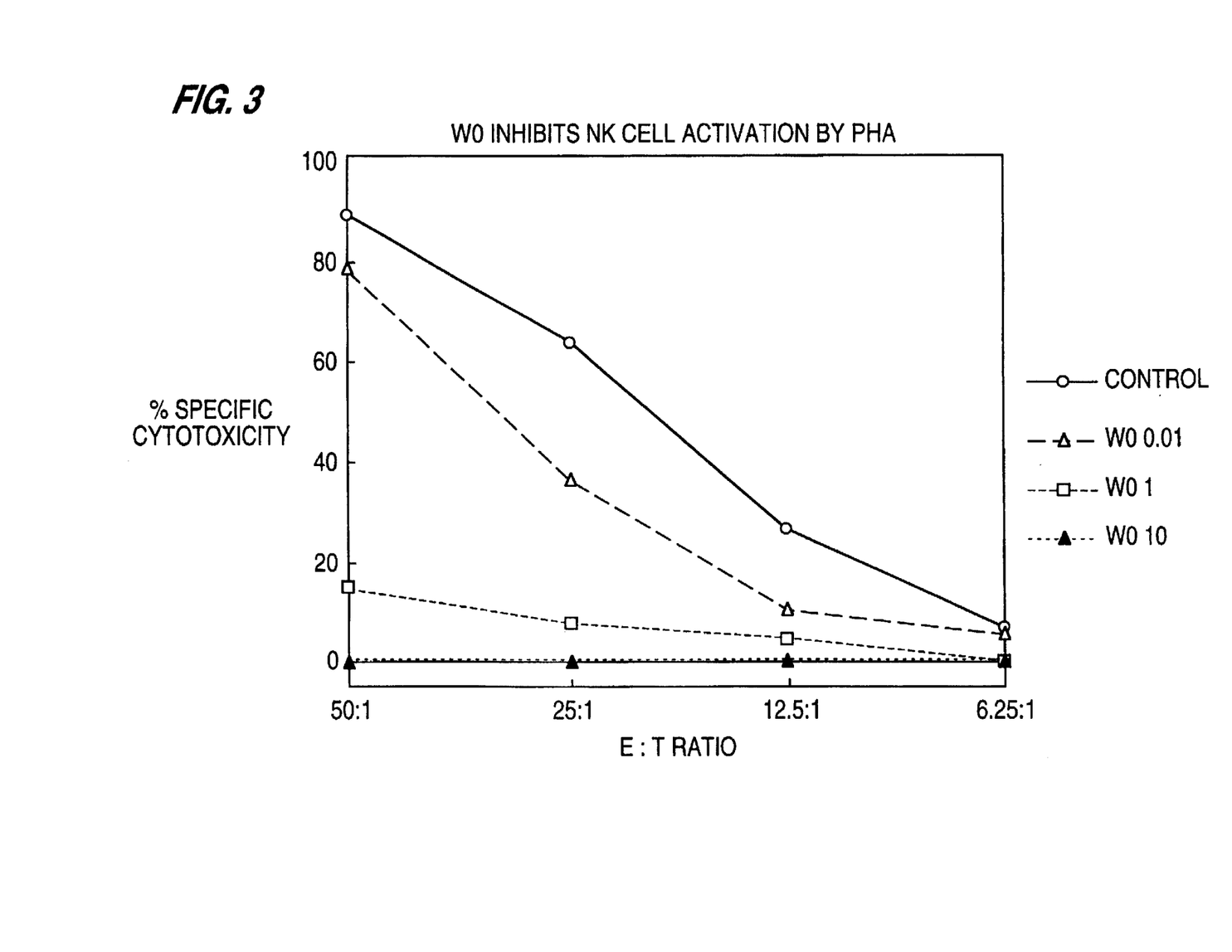
FIG. 3 is a graph showing that Withajardin A ("WO") inhibits activation of natural killer cells ("NK") cells by PHA. Specific cytotoxicity is displayed along the vertical axis in per cent. The effector target ratio ("E:T") is displayed along the horizontal axis. Results are shown for several concentrations of WO.

The absolute configuration of withajardin C was established by means of X-ray diffraction; a perspective view of the structure is shown in FIG. 3. The central ring system is formed by the fusion of one five-membered and three six-membered rings characterized by two trans-connected rings B/C and C/D and the quasi cis connected A/B rings, four axial substitutes, two methyl groups at C-10 and C-13 (β-position) and two hydroxy substituents at C-14 and C-17 (α-oriented); the protonated carbons C-8 and C-9 are α and β positioned, respectively. Rings A and B adopted a half-chair conformation and the C ring is chair conformed. The five-membered D-ring adopts a conformation between half-chair and envelope. This moity is linked to another ring system with three six-membered rings (C-20, C-21, C-25, C-26, O-5, C-22; C-20, C-21, C-25, C-24, C-23, C-22, C-23, C-24, C-25, C-26, O-5) all of which adopt a boat conformation; the protonated C-20 is β oriented and the molecule has several asymmetric centres with the following configurations: C-4 S, C-8 R, C-9 S, C-10 R, C-13 R, C-14 R, C-17 S, C-22 R, C-24 R, C-25 R.

The molecules are linked together in the crystal by hyrimgen hands between hydroxy groups and the water molecule. All hydroxy H atoms act as donors in one intermolecular H-bond and two intramolecular H-bonds. On the other hand, the water molecule acts as both donor and acceptor. The geometry of the H-bonds is described below:
Structure Solution The structure was solved by direct methods SIR88[19] and refined by full-matrix least-square methods with anisotropic thermal parameters for non-H atoms. All H-atoms were found in a Fourier difference map and were includes as isotropic contributors and refined. A weighting scheme was selected to prevent dependence in $w\Delta^2 F > vs < |Fu| > and < sin\theta/\lambda$. After several cycles of weighted mixed refinement, the final R and Rw values were 3.5 and 4.0, respectively. The final difference synthesis showed the residual electron density as no greater than 25 e Å$^{-3}$; number of variables 525, ratio of freedom 4.98, degree of freedom 2094. The absolute configuration was determined with Bijvoet differences with $\Delta Fo > 0.15$ add with the least experimental error Fo>10e (Fo). 37 more relevant Bijvoet pairs from the raw data (hkl and –h –k –l alternately measured intensities with no extra care on recentering, scan speed, etc) gave the following results: $R1 = \Sigma[\Delta Fo - \Delta Fe]/N = 0.316$ and $R2 = \Sigma[\Delta l - \Delta lc]/\Sigma[\Delta lo] = 0.879$ for the right enantiomer model, the R1 and R2 values for the wrong enantiomer were 0.476 and 1.273, respectively, thus the absolute configuration was established for the molecule.

Withajardin B(3) $C_{28}H_{38}O_8$, is a very similar compound to withajardin C, which can be deduced from the similarity of their $^1$H and $^{13}$C NMR spectra (Tables I and III), with only a few differences in the chemical shift, chiefly of H-4 and C-2, C-5. Moreover the $^1$H and $^{13}$C NMR spectra of withajardin B do not have the characteristic signals of the acetate group which in withajardin C was placed at C-4 by HMBC; therefore, withajardin B would seem to be 4-Hydroxy-4-deacetoxy-withajardin C. This is supported by the correlation of 4-OH with C-3, C-4 and C-5 (Table IV). To check out this theory, withajardin B was cold-acetylated and formed a monoacetate which proved identical to withajardin C in its IR and NMR spectra.

Withajardins A and D (1 and 2) seem also to be a very similar pair of compounds and are distinguished from the other two withajardins only by the presence of a double bond instead of an epoxide17, the rest of the molecule being the same. The position of the double bond between C-5, C-6 was established by means of HMBC since two and three-bond correlations of C-5 with H-3, H-4, H-8 and H-19 could be discerned (Table IV). The β configuration of the substituent at C-4 in both withanolides is similar to that of withajardins B and C and could be deduced by the chemical shift of Me-19 to a relatively low field[17,18] and by the presence of a ROESY effect between H-4 and H-6. The ROESY effect between Me-27 and Me-28 was no clearly visible due to the fact that both groups have a very similar chemical shift.

Withajardin A is a withanolide with a new nucleus of natural products, isolated from leaves and stems of *Deprea orinocensis* H.B.K. Its structure was defined by the displacements of the carbonyl group of the lactone in $^{13}$C NMR, found at 177.21 ppm which is a field lower than usual for withanolides.

Withajardin A: White Powder; HRMS m/z (rel int %) 448.2238 ($C_{28}H_{32}O_5$) (25), 450.2574 ($M^+$–2H$_2$O) (25), 432.2396, (35), 417.2125 (15), 280.1439 ($C_{19}H_{20}O_2$) (10), 238.1316 ($C_{17}H_{18}O$) (90), 125.1468 ($C_7H_9O_2$) (60), 55.00993 ($C_4H_7$) (100).

In vitro studies have shown that withajardin A has a dual effect on the proliferation of human peripheral blood lymphocytes induced by mitogens (PHA, Con A or PWM), alloantigens or microbial antigens (Purified protein derivative, PPD). At low doses (0.01 µg/ml) there is an increased in $^3$H-Thymidine incorporation, while at high concentrations (10 µg/ml) the proliferative response is completely inhibited.

Mononuclear cells obtained from healthy individuals were cultured for 72 h with either 1 µg/ml of PHA, 5 µg/ml of ConA or 10 µg/ml of PWM. Cultures of lymphocytes obtained from tuberculin positive healthy subjects were stimulated with 10 µ/ml of PPD and incubated for 120 h. Six to eight hours before harvesting the cultures were pulsed with 0.5 µCi/well of $^3$H-TDR.

Kinetics studies showed that withajardin A added during the first 24 h of culture is able to induce either stimulation or suppression of lymphocyte proliferation depending on the concentration used. Removal of withajardin A by washing and replacement with medium suggest that if withajardin A is present for 24 h or more its effects are irreversible.

Cell viability, as determined by tryptan blue exclusion, was always over 90% at 72 h of culture in the presence of withajardin A up to 10 µg/ml.

Withajardin A was able to inhibit IL-2 and IL-4 production by PHA stimulated lymphocytes in a dose dependant way.

The above discussion established that withajardins have a bicyclic lactone side chain with a six-membered homocycle which is different from the bicyclic system of the acnistins which consists of a five-membered homocycle, although the class of carbon atoms on $^{13}$C NMR is exactly the same for both types of substances. There are other differences, too, between withajardins and acnistins: the first have an extra hydroxyl at C-14 and the configuration of the side chain is 17β. The fact that acnistins have 17α configuration is abnormal in the withanolide field but has been accounted for by a biogenetic mechanism of dehydration-rehydroxylation[22] similar to that postulated[23] for the formation of 14 α-OH. The compounds obtained from *Deprea orinocensis* and *Dunalia solanaceae* suggest the existence of very specific enzymatic biogenetic mechanisms since, starting from a common precursor, only one type of substances forms in each species, which has been demostrated in our case by means of intensive phytochemical screening of both species. In no instance have withajardins and acnistins been encountered together. The biogenesis of all of these compounds may be explained as owing to a mechanism which requires prior oxidation of the me-21 (very possible in glycoside form) followed by an ⁻OH electrophilic attack on C-24 or C-25 depending on the species, and then a shift of the duble bond on the oxidized me-21.

This mechanism follows a different path from that for the formation of the withametelins[2] in which an electrophilic attack on 24,25-epoxy-withanolide takes place from the 21-$CH_2$ OH. Paradoxically, and in spite of a withanolide which does have 21-$CH_2$ OH having been obtained from Datura metel[12] (Whence the term withametelins), no other type of substance with a bicyclic system equal to that of the withajardins or acnistins has been reported to date from this species.

Physalin B, a type of substance obtained from other Solanaceae species such as Physalis or Witheringia[2] has also been found in *D. orinocensis* thus indicating an extra oxidative mechanism in this species at the me-18 level.

Despite the different positions of the hydroxy groups in relation to the lactone carbonyl group in acnistins and withajardins, the chemical shift in this latter is very similar in $^{13}C$ NMR in both types of compounds (Table I), although it is different from that of normal withanolides in which it appears at 166 ppm. In the case of acnistins this shift could be accounted for neighbouring β-hydroxylation. However in the withajardins there would seem to be other factors which notably influence the shift of the lactone carbonyl since the hydroxyl at C-24 in theory should exercise a effect on it, shifting it further upfield than normal. Such an effect may be cancelled out by the formation of H-bonding between the hydroxyls of C-24, C-17, and C-14 the presence of which has been firmly established, as seen above, by X-ray diffraction of withajardin C; in the same way, the generation of a bicyclic system with two six-membered rings apparently reduces the tension on the carbonyl which does not occur in the case of the acnistins. The chemical shift of Me-28, further upfield than expected for a hydroxy geminal group can be accounted for by it being situated in the unshielded zone of the lactone carbonyl.

Studies both with acnistins and with withajardins are under way to determine their immunomodulatory activity.

Experimental $^1H$ NMR spectra were recorded on a Bruker AM400 spectrometer at 400 MHz and $^{13}C$ NMR at 100 MHz; chemical shift are given in parts per million (δ) in relation to the solvent peaks. IR spectra were taken on a Perkin-Elmer Model 1600 spectrometer. Low-resolution mass spectra were run on a Hewlett-Packard 5995 and HRMS on a VG Micromass ZAB-2F, E1, 70 eV for withajardins A, B and D and 15 eV for withajardin C. Column chromatography was carried out on silica gel (Merck 0.2–0.5 nun) and TLC on silica gel plates, 0.25 mm, with visualization on oleum, heated to 120° C. The NMR data are given in tables I, III, IV and V.

Extraction and Isolation Procedures. *Deprea orinocensis* leaves (1.2 Kg) collected in El Jardin, Colombia in July 1991 were extractred by Soxhlet with hexane and then MeOH. The MeOH extract was evaporated almost to dryness, diluted with water and re-extracted with hexane (4×11) and EtOAc (6 l). The EtOAc extracts were chromatographed on silica gel with hexane-EtOAc (4:1–1:8) mixtures and 180 fractions, of 100 ml each were collected. Withajardin D (60 mg) and withajardin C (180 mg) were obtained from the less polar fractions and withajardins A (1.2 g) and B (800 mg) appeared after repeated column chromatography and/or crystallization on MeOH. The withajardins were detected by TLC due to the colour developed (blue or red) when the plates were sprayed and heated.

Withajardin A (1): white powder; HRMS m/z (rel int. %) 448.2238 ($C_{28}H_{32}O_5$) (25), 450.2574 ($M^+-2H_2O$) (25), 432.2396 (35), 417.2125 (15), 280.1439 ($C_{19}H_{20}O_2$) (10), 238.1316 ($C_{17}H_{18}O$) (90), 125.1468 ($C_7H_9O_2$) (60), 55.00993 ($C_4H_7$) (100).

Withajardin B (3): white powder; LRMS m/z (rel int. %) 487 ($M^+$–Me) (7), 450 (15), 432 (60), 399 (15), 249 (40), 238 (37), 171 (65), 125 (30), 107 (90), 91 (100), 55 (80).

Withajardin C (4): crystallzied from EtOH; HRMS m/z (rel int. %) 545.2747 ($M^+ +H^+$, $C_{30}H_{41}O_9$) (1), 484.2450 ($C_{28}H_{36}O_7$) (1), 254.1263 ($C_{17}H_{18}O_2$) (42), 238.1247 ($C_{13}H_{18}O_4$) (29), 173.0982 ($C_{12}H_{13}O$) (39), 124.0545 ($C_7H_8O_2$) (93), 55.0995 ($C_4H_7$) (100).

Crystal data. Formula $C_{30}H_{39}O_9 \cdot H_2O$. Molecular weight 545,648, calculated density 1.2971 g.cm$^{-1}$, μ=7.428 cm$^{-1}$, z=4. The compound crystallizes in the space group P212121. A suitable crystal of 0.35×0.30×0.20 mm. was used for data collection. Cell dimensions were determined by least-square from setting 38 reflections with 10°<θ<40°: a=27.934 (3), b=12.344, c=8.1032 (2) Å. The data were collected on a Philips PW 1100 diffractometer with graphite monochromated CuKα radiation. A total of 2753 independent reflections were measured and 2619 were considered as observed when I>2σ (I), and were used for the structure determination and refinement. Two reference reflections were checked every 90 treflections and they showed no intensity variation. The intensities measurements was performed up θ=65°, ω/2θ scan technique, scan speed 0.050 s.g$^{-1}$, scan width 1.60. With the same measurement time for both backgrounds as for the peak. The data were corrected for Lorentz and polarization effects, but not for absorption. The atomic scattering factors and the anomalous dispersion corrections were taken from the literature [24]. All calculations performed on a VAX 6410 and the programs from reference [20,21] and several local programs.

Withajardin D (2): white powder; LRMS m/z (rel int. %) 450 ($M^+$—HOAc—$H_2O$) (15), 432 (16), 249 (24), 238 (68), 223 (34), 197 (27), 171 (65), 125 (32), 109 (43), 69 (76), 55 (100).

The present invention is further described by reference to the following, illustrative examples.

EXAMPLE 1

Figure 1:
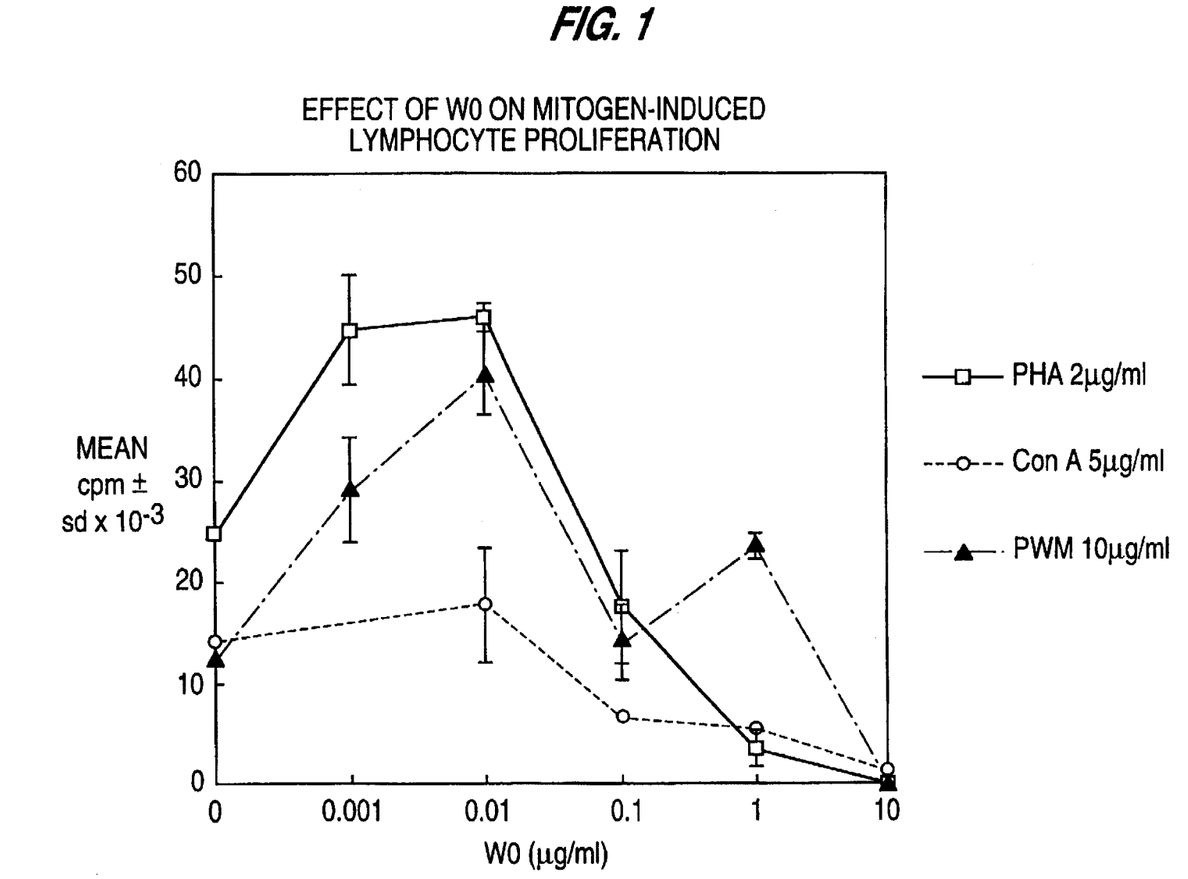
FIG. 1 is a graph showing the effect of a series of concentrations of Withajardin A ("WO") on the induction of lymphocyte (PBLs) proliferation by the mitogens PHA, Concanavalin A ("Con A") and pokeweed mitogen "PWM." Concentrations of Withajardin A ("WO") are displayed along the horizontal axis in micrograms per milliliter ("µg/ml"). Proliferative activity is measured by incorporation of $^3$H-thymidine in counts per minute ("cpm"), displayed along the vertical axis.

Withajardin A ("WO") stimulates at low concentrations and inhibits at high concentrations the induction of lymphocyte (PBL) proliferation by the mitogens PHA, Con A and PWM Peripheral blood lymphocytes were obtained and cultured by standard methods. The cells were incubated with phytohemagglutinin ("PHA"), concanavalin A ("Con A") and pokeweed mitogen ("PWM") at concentrations of 2, 5 and 10 μg/ml, respectively, and without WO, "0," or with WO at concentrations of 0.001, 0.01, 0.1, 1 and 10 μg/ml. Proliferative activity of the cells was measured by standard assay of $^3$H-thymidine is measured by incorporation. The results, expressed in counts per minute ("cpm"), are displayed in FIG. 1 and showed that WO stimulates mitogen-induced proliferation at low concentrations and inhibits it at higher concentrations.

EXAMPLE 2

Withajardin A ("WO") inhibits at high concentrations PPD-induced lymphocyte proliferation PBLs were obtained by standard methods from two patients suffering from tuberculosis infection (i.e., lymphocytes sensitized to the effects of PPD). The cells were incubated without WO, "0," and with WO at concentrations of 0.001, 0.01, 0.1, 1 and 10 µg/ml. Proliferative activity of the cells was measured by standard assay of $^3$H-thymidine is measured by incorporation. The results, displayed in FIG. 2 as counts per minute ("cpm") per cent of the control, showed that WO inhibits PPD-induced proliferation at the higher concentrations.

EXAMPLE 3

Withajardin A ("WO") inhibits NK cell activation by PHA in a dose-dependent manner NK cells were obtained and cultured by standard methods and incubated with PHA in presence and absence of Withajardin A ("WO"). NK cell activation was measured by standard cytotoxicity assay at a series of target ratios ("E:T" in FIG. 3.). The dose-dependent inhibition of PHA-activation of NK cells is shown in FIG. 3.

EXAMPLE 4

Withajardin ("WO") inhibits proliferation in mixed lymphocyte culture ("MLC")

Figure 4:
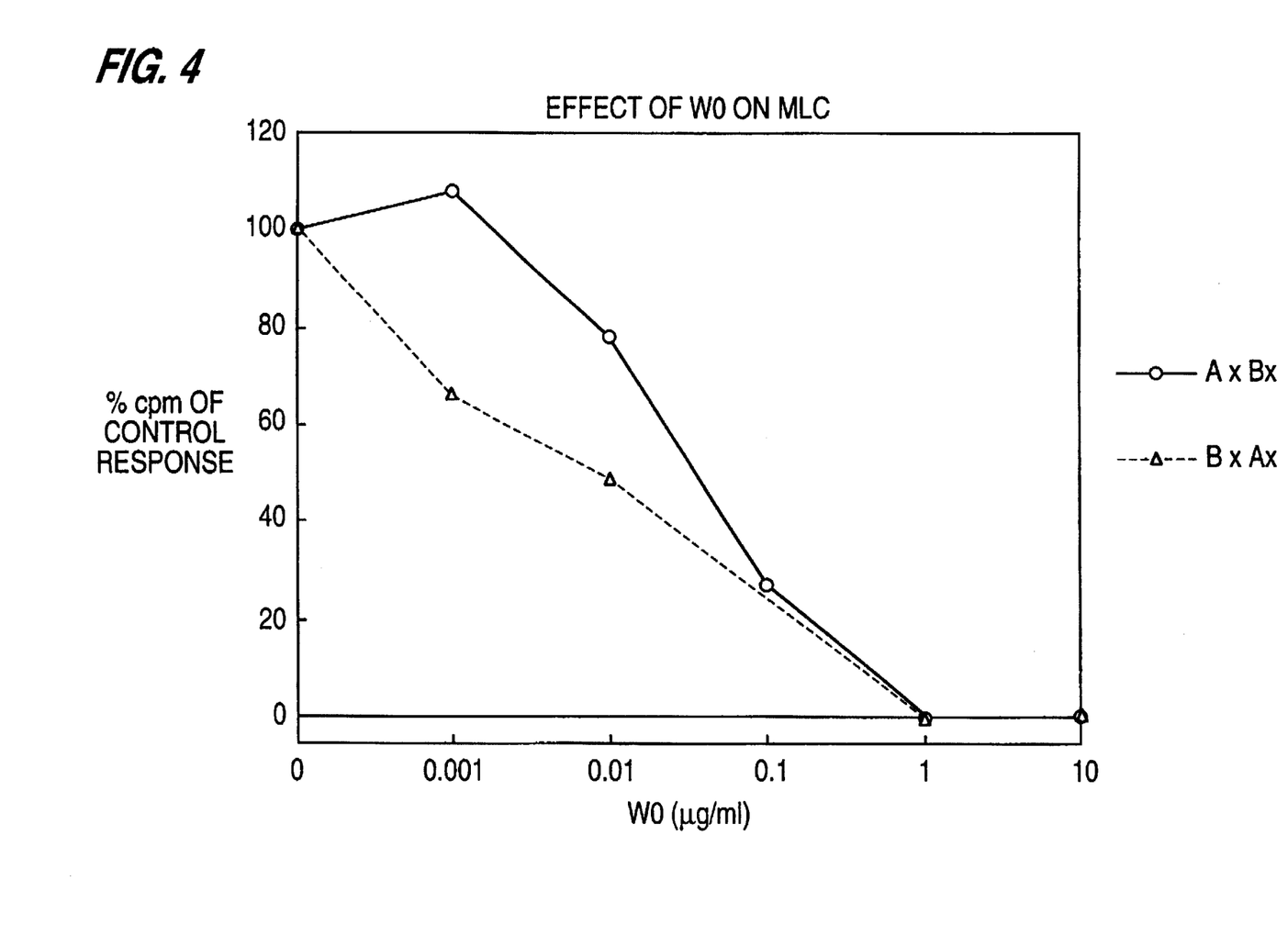
FIG. 4 is a graph showing the effect of a series of concentrations of Withajardin A ("WO") on proliferation of mixed lymphocyte cultures ("A×Bx and B×Ax"). A and B responder cells were stimulated by B or A cells pretreated with mitomycin C to block proliferation. (Pretreated cells are designated "Bx" and "Ax"). Concentrations of Withajardin A ("WO") are displayed along the horizontal axis in micrograms per milliliter ("µg/ml"). Proliferative activity as measured by incorporation of $^3$H-thymidine in counts per minute is displayed along the vertical axis as a per cent of the control response ("% cpm").

Mixed lymphocyte culture were prepared and cultured by standard methods. The results for two samples, "A" and "B," are shown in FIG. 4. The A or B responder cells were stimulated by B or A cells, respectively, which had been pretreated with mitomycin C to block proliferation (the pretreated cells are designated "Bx" and "Ax" in FIG. 4). The inhibitory effect of WO is seen in the plot based on thymidine incorporation set out in FIG. 4.

EXAMPLE 5

Withajardin ("WO") inhibits the generation of cytotoxic lymphocytes ("CTL") in mixed lymphocyte culture ("MLC")

Figure 5:
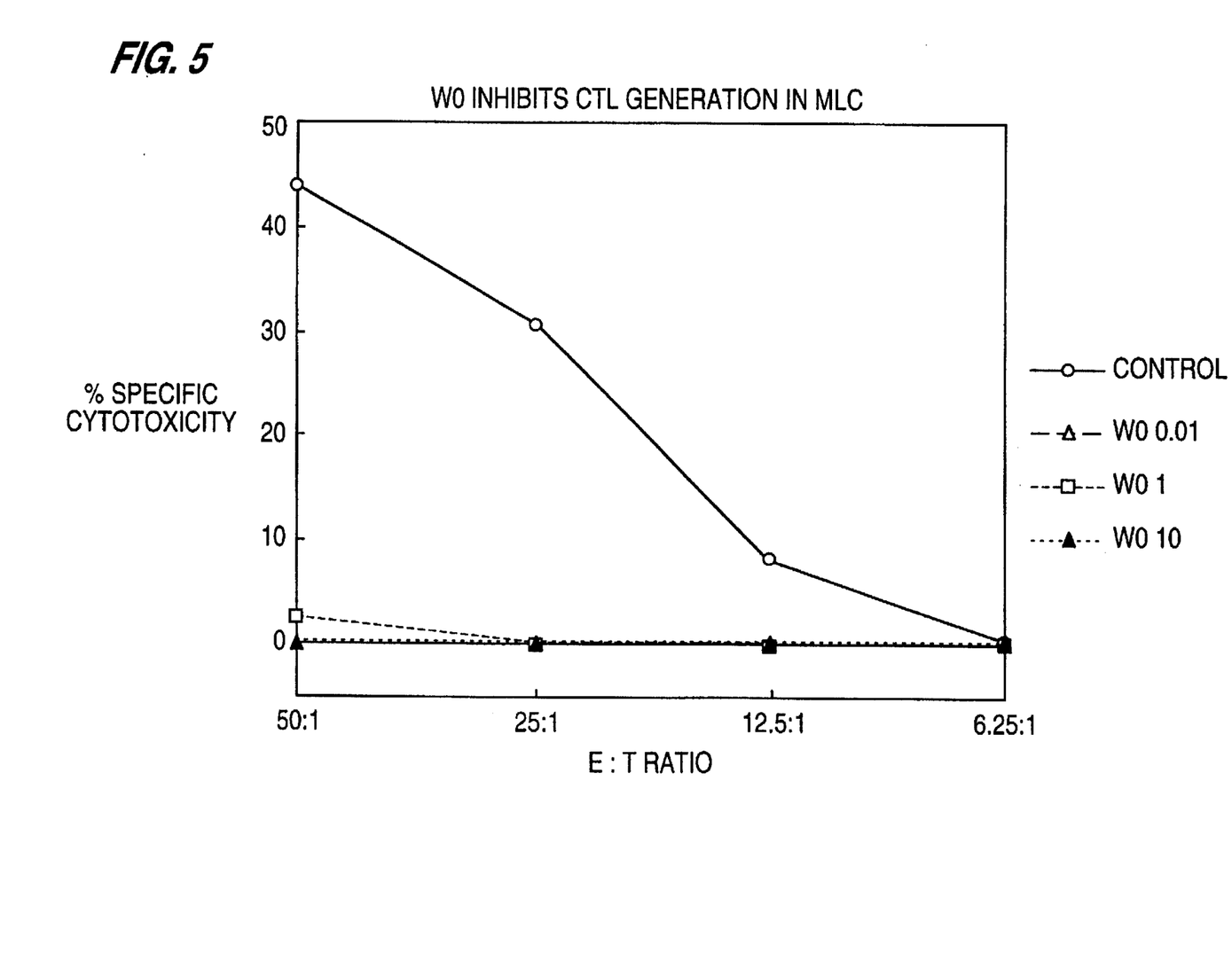
FIG. 5 is a graph showing that Withajardin A ("WO") inhibits the generation of cytotoxic lymphocytes ("CTL") in mixed lymphocyte culture ("MLC"). Specific cytotoxicity is displayed along the vertical axis in per cent. The effector target ratio ("E:T") is displayed along the horizontal axis.

The effects of WO on CTL generation in MLC was determined as described above for PHA-mediated NK cell activation in Example 3. As shown in FIG. 5, WO inhibits CTL generation at the tested concentrations.

EXAMPLE 6

Withajardin ("WO") inhibits natural killer cell ("NK") activity.

Figure 6:
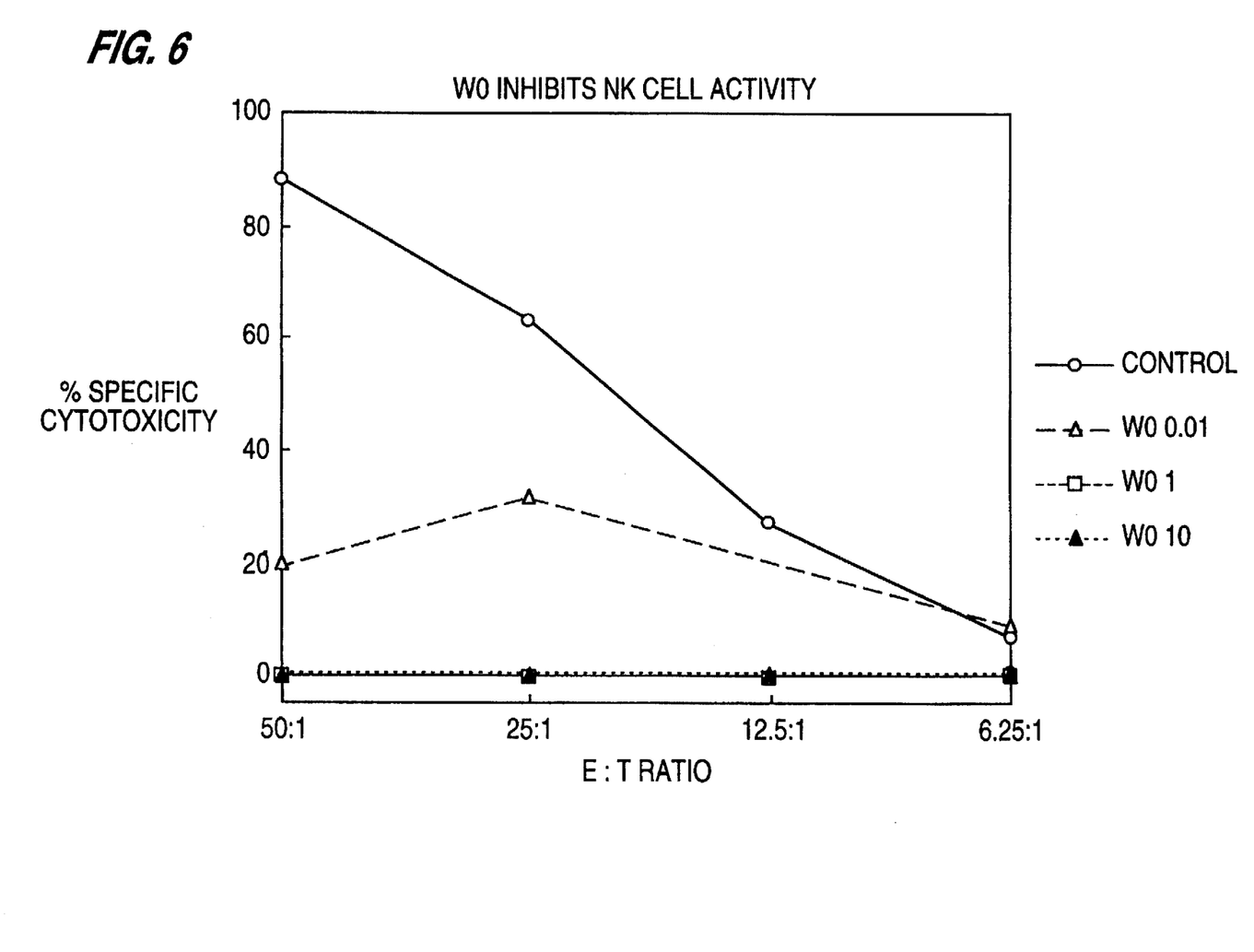
FIG. 6 is a graph showing that Withajardin A ("WO") inhibits natural killer cell ("NK") activity. Specific cytotoxicity is displayed along the vertical axis in per cent. The effector target ratio ("E:T") is displayed along the horizontal axis.

Experiments similar to those set out in Examples 5 and 3, with the results set out in FIG. 6, showed that WO inhibits NK cell activity in a dose-dependent manner.

EXAMPLE 7

Withajardin ("WO") inhibits cytotoxic lymphocyte ("CTL") activity

Figure 7:
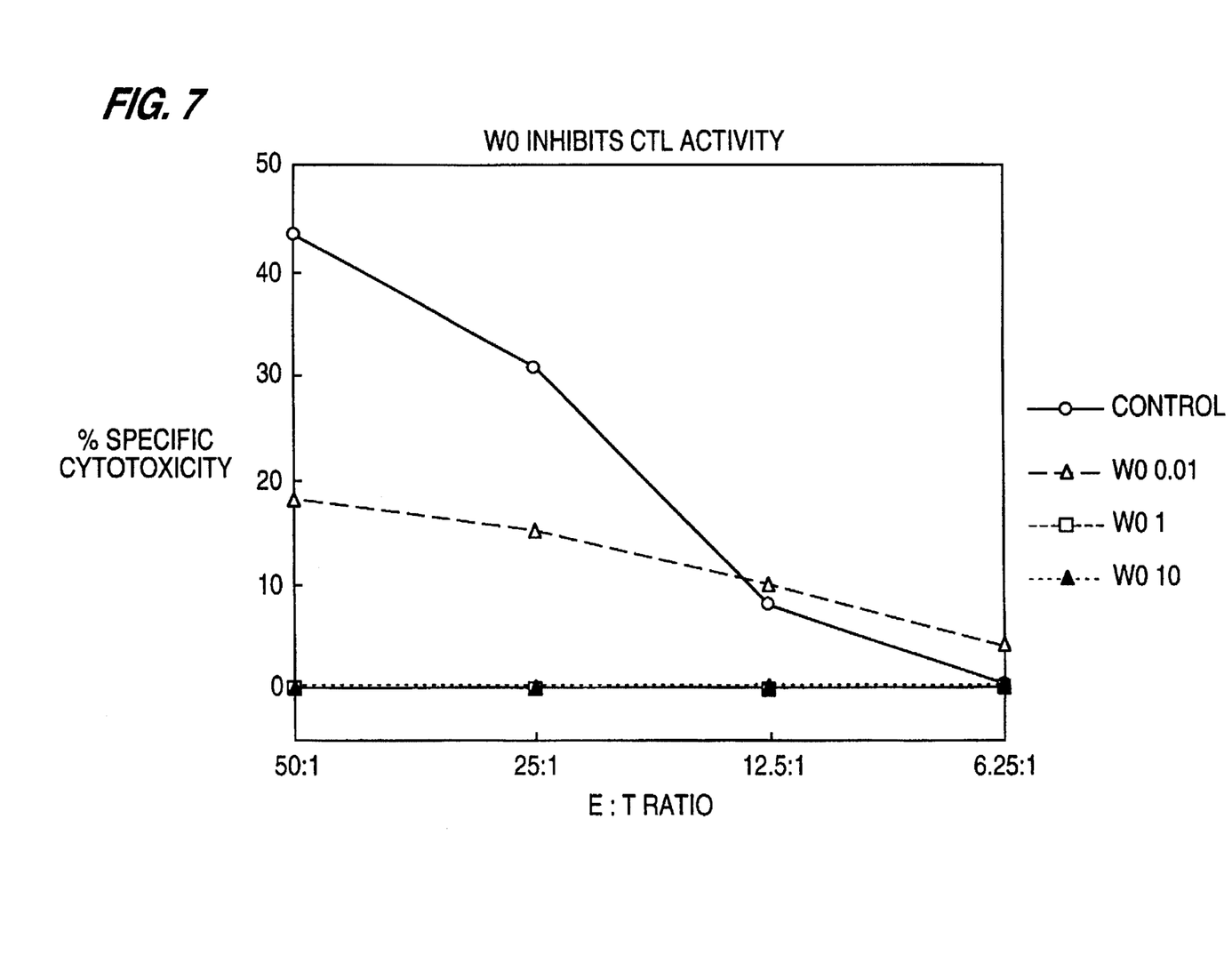
FIG. 7 is a graph showing that Withajardin A ("WO") inhibits cytotoxic lymphocyte ("CTL") activity. Specific cytotoxicity is displayed along the vertical axis in per cent. The effector target ratio ("E:T") is displayed along the horizontal axis.

Experiments similar to those set out in Examples 3, 5 and 6 were performed with the results set out in FIG. 7 and showed that WO inhibits CTL activity in a dose-dependent manner.

EXAMPLE 8

Withajardin ("WO") inhibits nitrate production by macrophage cells in absence and the presence of LPS ("+LPS")

Figure 8:
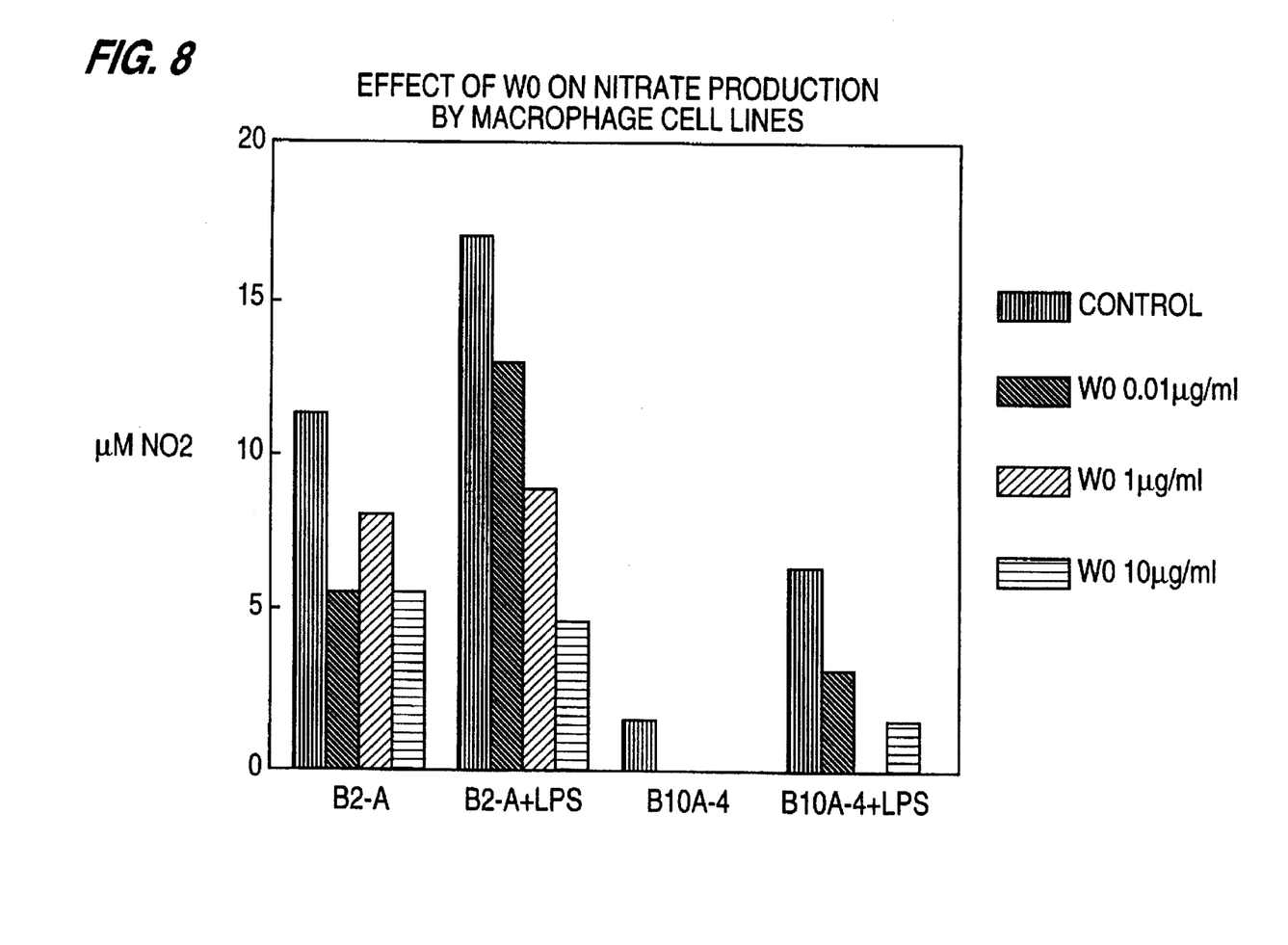
FIG. 8 is a graph showing the effect of Withajardin A ("WO") on nitrate production by the macrophage cells lines B2-A and B10-A4 in absence and the presence of LPS ("+LPS"). $NO_2$ production is displayed along the vertical axis in µM. The graph shows the results obtained at several WO concentrations as indicated on the left.

Macrophage cells were cultured by standard methods in the absence and presence of LPS (lipopolysaccharide) and the absence or presence at various concentrations of WO. The results, shown in FIG. 8, demonstrate that WO dose-dependently inhibits nitrate production in the presence and absence of LPS.

Figure 9:
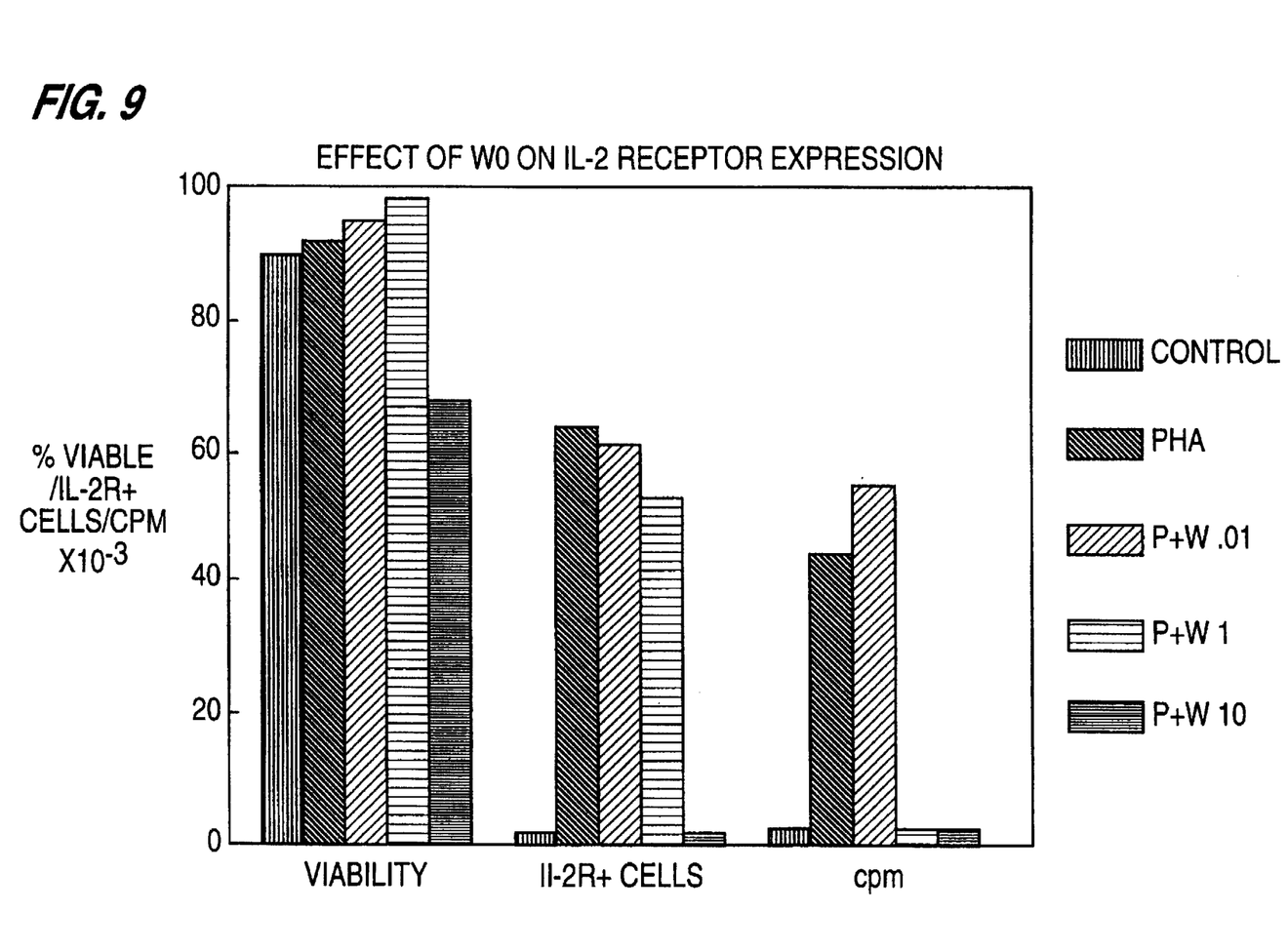
FIG. 9 is a graph showing the effect of Withajardin A ("WO") on expression of the interleukin-2 receptor ("IL-2R").

EXAMPLE 9 shows that Withajardin A ("WO") inhibits expression of the interleukin-2 receptor ("IL-2R") in PHA-stimulated cells IL-2-receptor expression was measured by standard methods in control and PHA-stimulated cells. The cells were tested for viability, as well. The results are shown in FIG. 9.

EXAMPLE 10

Figure 10:
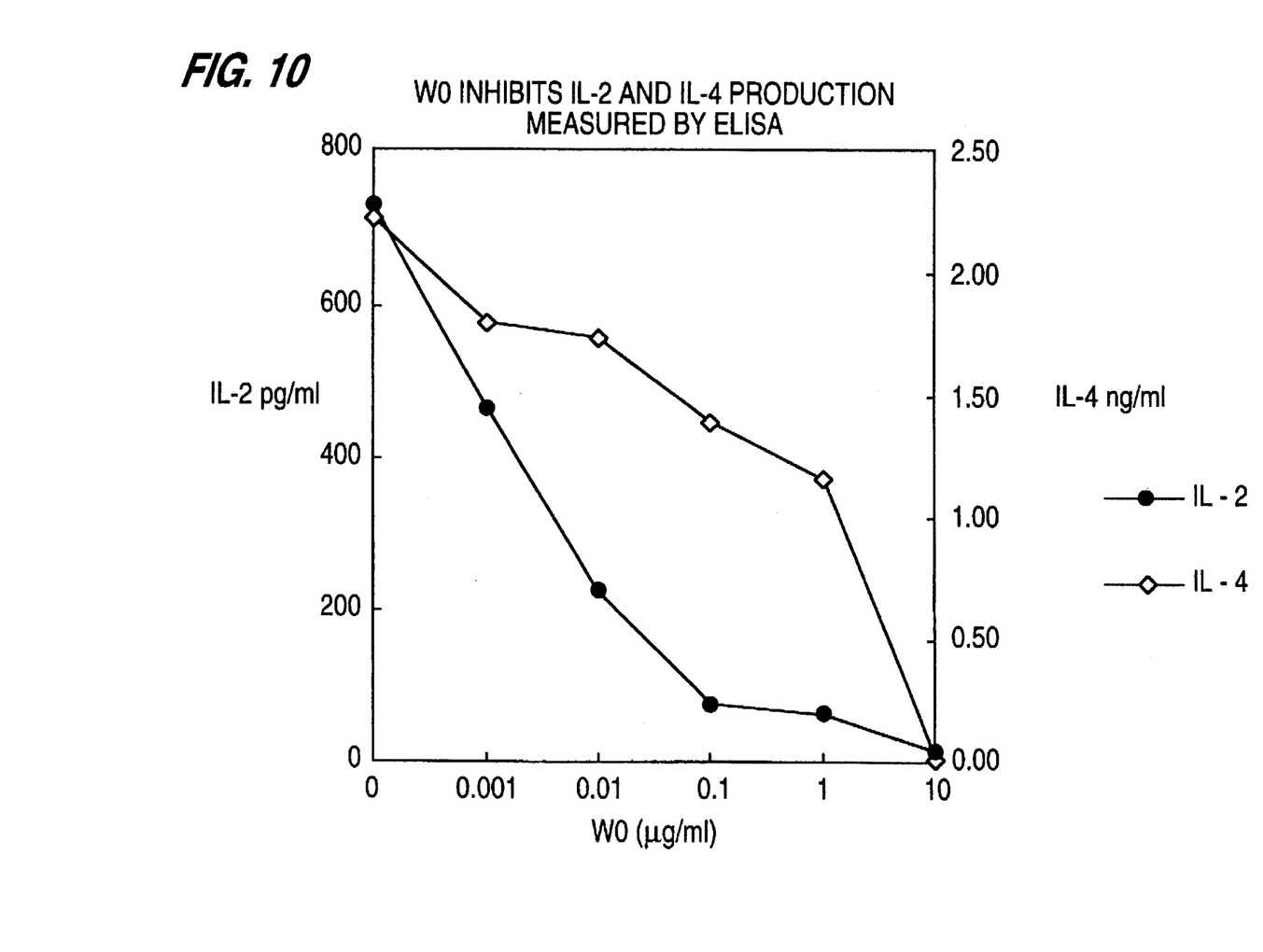
FIG. 10 is a graph showing that Withajardin A ("WO") inhibits expression of interleukin-2 ("IL-2") and interleukin-2 ("IL-2") in a dose-dependent manner. IL-2 and IL-4 were determined by a standard ELISA method.

Withajardin A ("WO") inhibits IL-2 and IL-4 production. Cells were obtained and cultured by standard methods for IL-2 and IL-4 assay and incubated in the absence and in the presence of various concentrations of WO. IL-2 and IL-4 production were measured by standard ELISA using a commercially available kit. As shown in FIG. 10, WO inhibits the production of both interleukins in a dose-dependent manner.

TABLE 1

$^{13}$C NMR of Withajardins A–D (1–4) and Acnistins A (5) and E (6)

| | Withajardins | | | | Acnistins | |
|---|---|---|---|---|---|---|
| Carbon | A (1)[a] | D (2)[b] | B (3)[a] | C (4)[b] | A (5)[b] | E (6)[b] |
| 1 | 203.23 s | 202.39 s | 201.64 s | 200.61 s | 202.36 s | 202.37 s |
| 2 | 127.40 d | 130.83 d | 131.28 d | 133.73 d | 129.87 d | 133.08 d |
| 3 | 146.15 d | 140.00 d | 145.06 d | 139.70 d | 143.56 d | 141.31 d |
| 4 | 67.38 d | 70.20 d | 68.59 d | 71.32 d | 31.00 t | 70.27 d |
| 5 | 138.09 s | 134.33 s | 63.01 s | 60.91 s | 62.14 s | 64.02 s |
| 6 | 128.75 d | 133.16 d | 59.22 d | 60.73 d | 62.89 d | 61.69 d |
| 7 | 24.38 t | 25.01 t | 24.91 t | 25.75 t | 32.76 t | 30.92 t |
| 8 | 35.77 d | 36.15 d | 33.32 d | 35.98 d | 30.74 d | 30.72 d |
| 9 | 35.86 d | 36.32 d | 36.81 d | 37.41 d | 43.85 d | 43.14 d |
| 10 | 48.78 s | 49.36 s | 47.07 s | 47.62 s | 46.94 s | 47.85 s |

TABLE 1-continued

$^{13}$C NMR of Withajardins A–D (1–4) and Acnistins A (5) and E (6)

| Carbon | Withajardins | | | | Acnistins | |
|---|---|---|---|---|---|---|
| | A (1)[a] | D (2)[b] | B (3)[a] | C (4)[b] | A (5)[b] | E (6)[b] |
| 11 | 21.17 t | 21.51 t | 19.33 t | 20.87 t | 22.69 t | 21.52 t |
| 12 | 26.13 t | 26.41 t | 25.24 t | 25.31 t | 33.26 t | 32.97 t |
| 13 | 49.95 s | 50.67 s | 49.95 s | 50.60 s | 48.54 s | 46.80 s |
| 14 | 85.21 s | 86.80 s | 85.09 s | 86.90 s | 50.42 d | 50.71 d |
| 15 | 32.15 t | 33.70 t | 32.11 t | 33.52 t | 23.50 t | 23.96 t |
| 16 | 35.73 t | 35.90 t | 35.93 t | 35.92 t | 36.92 t | 36.69 t |
| 17 | 84.26 s | 85.09 s | 84.18 s | 85.09 s | 85.43 s | 85.07 s |
| 18 | 18.92 q | 19.91 q | 18.51 q | 19.60 q | 14.41 q | 14.00 q |
| 19 | 21.85 q | 21.36 q | 16.10 q | 15.98 q | 14.20 q | 16.57 q |
| 20 | 41.85 d | 41.25 d | 41.96 d | 41.25 d | 51.33 d | 51.36 d |
| 21 | 26.00 t | 27.12 t | 26.00 t | 27.09 t | 37.09 t | 37.13 t |
| 22 | 76.54 d | 77.00 t | 76.46 d | 77.10 d | 84.05 d | 84.03 d |
| 23 | 40.93 t | 41.67 t | 40.83 t | 41.67 t | 41.20 t | 41.22 t |
| 24 | 69.53 s | 70.27 s | 69.55 s | 70.30 s | 45.30 s | 45.35 s |
| 25 | 47.28 s | 47.80 s | 47.27 s | 47.91 s | 76.63 s | 76.70 s |
| 26 | 177.21 s | 178.29 s | 177.15 s | 178.80 s | 179.09 s | 178.92 s |
| 27 | 14.47 q | 14.44 s | 14.46 q | 14.52 q | 25.55 q | 25.56 q |
| 28 | 27.67 q | 27.49 s | 27.68 q | 27.57 q | 19.92 q | 19.89 q |
| MeCOO | | 170.20 s | | 170.10 s | | |
| MeCOO | | 21.61 q | | 19.91 s | | |

[a]: Recorded at 100.0 MHz, DMSO-d6.
[b]: Recorded at 100.0 MHz, CDCl$_3$. Multiplicities were determined by DEPT experiments.

TABLE II

Mass, IR Spectra and mps. of Withajardins 1–4

| Compound | Formula | Highest Mass ions observed[a] | IR, cm$^{-1}$ | m.p., °C. |
|---|---|---|---|---|
| Withajardin A (1) | C$_{28}$O$_{38}$O$_7$ | 450.2574<br>450.2568 (M$^+$—H$_2$O) | 3300,1725,1660 | 225, descomp. |
| Withajardin B (3) | C$_{28}$H$_{38}$O$_8$ | 487 (M$^+$—Me) | 3400,1730,1665 | 228, descomp. |
| Withajardin C (4) | C$_{30}$H$_{40}$O$_9$ | 545.2747<br>545.2769 (M$^+$ + H$^+$) | 3450,1740,1725,1660 | 268, descomp. |
| Withajardin D (2) | C$_{30}$H$_{40}$O$_8$ | 450 (M$^+$—AcOH—H$_2$O) | 3350,1735,1725,1660 | 182, descomp. |

[a]: Observed/Calculated for specific formula. I.E., 70 eV, except for withajardin C, 15 eV

TABLE III

$^1$H NMR of Withajardins A–D (1–4)

| H | Withajardin A(1)[a] | Withajardin D(2)[b] | Withajardin B(3)[a] | Withajardin C(4)[b] |
|---|---|---|---|---|
| 2 | 5.81 (d, 4.3) | 6.01 (d, 10.0) | 6.15 (d, 9.8) | 6.25 (d, 9.8) |
| 3 | 6.81 (dd, 4.6, 10.0) | 6.69 (dd, 4.7, 10.0) | 7.07 (dd, 6.3, 9.8) | 7.00 (dd, 6.0, 9.8) |
| 4 | 4.55 (t, 4.5) | 5.76 (d, 4.7) | 3.55 (dd, 4.3, 6.1) | 4.62 (d, 6.0) |
| 6 | 6.82 (d, 4.2) | 6.09 (d, 2.8) | 3.24 (brs, 4.5) | 3.30 (brs, 5.0) |
| 7-ax | 2.09 (dd, 3.8, 18.6) | 1.95 (m) | 1.98 (dt, 4.7, 17.0) | 2.5 (d, 11.8) |
| 7-eq | 1.21 (d, 14.29) | | 1.16 (d, 13.6) | 1.25 (d, 13.7) |
| 8 | 1.75 (m) | 1.82 (m) | 1.67 (m) | 1.80 (m) |
| 9 | 1.50 (m) | 1.42 (m) | 1.40 (m) | 1.57 (m) |
| 11-ax | | 1.89 (m) | 1.90 (m) | 1.90 (m) |
| 11-eq | 1.56 (dd, 4.7, 10.2) | | 1.54 (m) | 1.64 (dd, 4.5, 11.0) |
| 12-ax | 1.81 (m) | 1.78 (m) | 1.80 (m) | 1.90 (m) |
| 12-eq | 1.60 (m) | 1.61 (m) | 1.61 (m) | 1.62 (m) |
| 15-β | 1.78 (m) | 1.75 (m) | 1.76 (m) | 1.74 (m) |
| 15-α | 1.47 (dd, 4.2, 11.0) | 1.46 (m) | 1.45 (m) | 1.47 (dd, 4.3, 13.0) |
| 16-β | 1.99 (dq, 4.2, 11.5, 16.3) | 1.89 (m) | 2.15 (m) | 2.15 (m) |
| 16-α | 1.77 (m) | 2.05 (m) | | 1.82 (m) |
| 18 | 0.84 (s) | 0.89 (s) | 0.79 (s) | 0.86 (s) |
| 19 | 1.33 (s) | 1.39 (s) | 1.30 (s) | 1.41 (s) |
| 20 | 2.24 (m) | 2.25 (m) | 2.28 (m) | 2.25 (m) |
| 21-ax | 2.16 (d, 13.4) | 2.18 (m) | 2.28 (m) | 2.18 (m) |
| 21-eq | 1.40 (dd, 1.9, 11.6) | 1.45 (m) | 1.50 (m) | 1.47 (d, 12.2) |

TABLE III-continued

$^1$H NMR of Withajardins A–D (1–4)

| H | Withajardin A(1)[a] | Withajardin D(2)[b] | Withajardin B(3)[a] | Withajardin C(4)[b] |
|---|---|---|---|---|
| 22 | 4.62 (brs, 6.0) | 4.61 (brs, 6.0) | 4.62 (brs, 6.0) | 4.62 (d, 1.7) |
| 23-ax | 2.42 (d, 14.4) | 2.46 (d, 15.0) | 2.42 (d, 14.6) | 2.44 (d, 13.7) |
| 23-eq | 1.85 (m) | 1.85 (m) | 1.82 (m) | 1.87 (m) |
| 27 | 0.97 (s) | 1.09 (s) | 0.97 (s) | 1.11 (s) |
| 28 | 0.98 (s) | 1.09 (s) | 0.99 (s) | 1.13 (s) |
| MeCOO | | 2.08 (s) | | 2.05 (s) |
| 4-OH | 5.43 (d, 4.4) | | 5.58 (d, 4.2) | |
| 14-OH | 5.34 (d, 6.3) | 3.16 (s) | 5.39 (s) | 3.02 (s) |
| 17-OH | 6.43 (t, 5.1)) | 6.18 (s) | 6.84 (s) | 6.18 (s) |
| 24-OH | 4.03 (d, 7.2) | 5.21 (s) | 4.90 (s) | 5.21 (s) |

[a]DMSO-d$_6$.
[b]CDCl$_3$. Scalar coupling constants, were determined from HOMO-2D-J and ROESY spectroscopy.

TABLE IV

Three and Two Bond Correlations (HMBC Experiment) of Withajardins A–D (1–4)[a]

| C | Withajardin A(1)[b] | Withajardin D(2)[c] | Withajardin B(3)[b] | Withajardin C(4)[c] |
|---|---|---|---|---|
| 1 | 19-Me | 3, 19-Me | 2, 3, 19-Me | 19-Me |
| 2 | | | | 4 |
| 3 | | 4 | 4, 5, 4-OH | 4 |
| 4 | | 2 | 2, 3, 4-OH | 2, 3 |
| 5 | 19-Me | 3, 4, 19-Me | 4, 4-OH, 19-Me | 3, 4, 7, 19-Me |
| 6 | | 8 | | |
| 7 | | | 6 | 6 |
| 8 | | | 6 | 6 |
| 9 | 19-Me | 19-Me | 7, 19-Me | 19-Me |
| 10 | 2, 6, 19-Me | 2, 4, 6, 19-Me | 2, 4, 19-Me | 2, 4, 19-Me |
| 12 | | 18-Me | 18-Me | 18-Me |
| 13 | 14-OH, 18-Me | 14-OH, 18-Me | 14-OH, 18-Me | 18-Me |
| 14 | | 18-Me | 18-Me | 18-Me |
| 15 | | 8, 14-OH | | |
| 16 | | 20 | — | 15-β |
| 17 | 18-Me | 17-OH, 20, 21-ax | 17-OH, 21-ax | 18-Me, 21-ax |
| 20 | 17-OH | 17-OH, 21ax | 17-OH | |
| 21 | 28-Me | 27-Me | 27-Me | 27-Me |
| 23 | 28-Me | 28-Me | 28-Me | 20,-24-OH |
| 24 | 23-ax, 25-OH, 27-Me | 21-ax, 23, 24-OH | 23-ax, 24-OH, 28-Me | 21-eq, 21-ax, 23-ax, 28-Me |
| 25 | 28-Me | 21-ax, 28-Me | 21-ax, 23-ax, 24-OH, 27-Me | 28-Me |
| 26 | 27-Me | 21-ax, 27-Me | 12-ax, 22 | 21-ax, 22, 27-Me |
| 28 | 24-OH | 24-OH | 24-OH | |
| Me—COO— | | 4, Me—COO— | | |
| Me—COO— | | | | 4, Me—COO |

TABLE V

ROESY Correlations for Withajardins

| Proton | withajardin A(1) | withajardin D(2) | withajardin B(3) | withajardin C(4) |
|---|---|---|---|---|
| H-2 | H-3 | H-3 | H-3 | H-3 |
| H-3 | H-2, 4-OH | H-2, H-4, 4-OH | | |
| H-4 | H-6, 4-OH | H-3, H-6, 4-OH | | |
| H-6 | H-4, H-7ax | H-3 | H-4 | H-3 |
| H-8 | 19-Me | 19-Me | 19-Me | 19-Me |
| H-11ax | 19-Me | 19-Me, H-12eq | | |
| H-16α | H-21eq, H-23eq | H-23eq | H-21eq | H-23eq |
| H-20 | 18-Me, H-21eq | H-23eq | 18-Me, H-21eq | H-23eq |
| H-21ax | H-21eq, H-22 | H-21eq, H-22, 24-OH | H-22, 17-OH, 24-OH | H-21eq, H-22 |
| H-21eq | H-16α, 27-Me | H-16α, 27-Me | H-16α, 27-Me | |
| H-22 | H-20, H-23eq, H-23ax | H-20, H-21ax, H-21eq | H-20, H23aq, H-23ax | H-20, H-21ax, H-21eq |
| H-23ax | H-16α, 24-OH | H-22, H-23eq, 18-Me | H-16α, 24-OH | H-21eq, H-23eq, 18-Me |
| 24-OH | H-21ax, H-23ax, 17-OH, 27-Me | H-21ax, H-23ax, 17-OH | H-21ax, H-23ax | H-21ax, H-23ax |

TABLE V-continued

ROESY Correlations for Withajardins

| Proton | withaiardin A(1) | withaiardin D(2) | withaiardin B(3) | withaiardin C(4) |
|---|---|---|---|---|
| 17-OH | 14-OH, 24-OH | 14-OH, 24-OH | | |
| 4-OH | H-3, H-4 | H-3, H-4 | | |

REFERENCES

1. Kirson I., Glotter E. *J. Nat. Prod.* (1981) 44, 633
2. Glotter E. *Nat. Prod. Rep.* (1991) 8, 415
3. Ksebati M. B., Schmitz .J. *J. Org. Chem.* (1988) 53, 3926
4. Kupchan S. M., Anderson W. K., Bollinger P., Doskotch R. W., Smith R. M., Saenz-Renauld J., Schnoes H., Burlingame A. L., Smith D. H. *J. Org. Chem.* (1969) 34, 3858
5. Suffness M., Douros J. *J. Nat. Prod.* (1981) 45, 1
6. Shohat K., Kirson I., Lavie D. *Biomedicine* (1978) 28, 18.
7. Budhiraja R., Sudhir G., Gard K. *Planta Medica* (1984) 50, 134
8. Budhiraja R., Sudhir G., Gard K., Arora B. *Planta Medica* (1986) 52, 28
9. Kawai M., Ogura T., Makino B., Matsumoto K., Yamamura H., Butsugan Y., Hayashi H. *Phytochemistry* (1992) 31, 4299
10. Lavie D., Besalle R., Pestchanker M., Gottlieb H. E., Frolow F., Giordano O. S. *Phytochemistry* (1987) 26, 1791
11. Fajardo V., Podesta F., Shamma M., Freyer A. *J.Nat. Prod.* (1991) 54, 554
12. Gupta M., Manickam M., Sinha-Bagchi A., Ray A. *Phytochemistry* (1992) 31, 2324
13. Usubillaga A., Castellano G., Zabel V., Watson W. H. *J. Chem. Soc. Chem. Commun.* (1980) 854
14. Luis J. G., Echeverri F., Quiñones W., González A. G., Torres F., Cardona G., Archbold R., Perales A. *Steroids* (in press).
15. Bax A., Sommer M. F. *J. Am. Chem. Soc.* (1986) 108, 2093
16. Bax A., Subramanian S. *J. Magn. Reson.* (1986) 67, 565
17. Gottlieb H. E., Kirson I. *Org. Magn. Reson.* (1981) 16, 20
18. Pelletier S. W., Mody N. V., Nowacki J., Bhattacharyya J. *J. Nat. Prod.* (1979) 42, 512
19. SIR88. A direct-methods program for the automatic solution of crystal structure. Burla M. C., Camalli M. Cascarano G., Giacovazzo C., Polidori G., Spagna R. and Viterbo V. *J. Appl. Cryst.* (1989) 22 389–393.
20. Stewart J. M., Machin P. A., Dickinson D. W., Ammon H. L., Heck G. and Flak H. Y.(1976). The X-ray-76 System. *Tech. Rep.* TR446, Computer Science Center, University of Maryland, USA.
21. Motherwell W. D. S. and Clegg W. (1978) PLUTO. Program for plotting molecular and crystal structures. Univ. Cambridge, England.
22. Van de Velde V., Lavie D. *Phytochemistry* (1981) 20, 1359
23. Nittala S., Lavie D. *Phytochemistry* (1981) 20, 2741
24. International Tables for X-ray Crystalography (1974) V, IV, Kynoch Press, Birmingham, England.

What is claimed is:

1. A compound having the structure I:

wherein:

Y is O or a double bond; and R is OH, lower acyloxy, lower alkoxy or lower alkyl.

2. The compound of claim 1, wherein Y is O.
3. The compound of claim 1, wherein Y is a double bond.
4. The compound of claim 2, wherein R is OH.
5. The compound of claim 2, wherein R is acetoxy.
6. The compound of claim 3, wherein R is OH.
7. The compound of claim 3, wherein R is acetoxy.
8. The compound of claim 1, wherein R is methyl.
9. The compound of claim 1, wherein R is methoxy.

* * * * *